(12) United States Patent
Hepler et al.

(10) Patent No.: US 11,986,483 B2
(45) Date of Patent: May 21, 2024

(54) OTIC FORMULATIONS, METHODS AND DEVICES

(71) Applicant: Dechra Veterinary Products, LLC, Overland Park, KS (US)

(72) Inventors: Douglas I. Hepler, Overland Park, KS (US); Gail L. Dempsey, Overland Park, KS (US); Dorothea A. Erxleben, Overland Park, KS (US); Neil E. Paulsen, Overland Park, KS (US)

(73) Assignee: Dechra Veterinary Products, LLC, Overland Park, KS (US)

( * ) Notice: Subject to any disclaimer, the term of this patent is extended or adjusted under 35 U.S.C. 154(b) by 99 days.

(21) Appl. No.: 17/066,343

(22) Filed: Oct. 8, 2020

(65) Prior Publication Data

US 2021/0106597 A1 Apr. 15, 2021

Related U.S. Application Data

(60) Provisional application No. 62/914,301, filed on Oct. 11, 2019.

(51) Int. Cl.

| | |
|---|---|
| *A61K 31/573* | (2006.01) |
| *A61D 7/00* | (2006.01) |
| *A61K 9/00* | (2006.01) |
| *A61K 31/137* | (2006.01) |
| *A61K 31/4174* | (2006.01) |
| *A61K 31/5395* | (2006.01) |
| *A61K 31/56* | (2006.01) |
| *A61K 31/58* | (2006.01) |
| *A61K 47/44* | (2017.01) |
| *A61M 31/00* | (2006.01) |
| *A61P 27/16* | (2006.01) |
| *A61P 31/00* | (2006.01) |

(52) U.S. Cl.
CPC ............ *A61K 31/573* (2013.01); *A61D 7/00* (2013.01); *A61K 9/0046* (2013.01); *A61K 31/137* (2013.01); *A61K 31/4174* (2013.01); *A61K 31/5395* (2013.01); *A61K 31/56* (2013.01); *A61K 31/58* (2013.01); *A61K 47/44* (2013.01); *A61M 31/00* (2013.01); *A61P 27/16* (2018.01); *A61P 31/00* (2018.01); *A61M 2210/0662* (2013.01)

(58) Field of Classification Search
CPC .. A61K 31/573; A61K 9/0046; A61K 31/137; A61K 31/4174; A61K 31/5395; A61K 31/56; A61K 31/58; A61K 47/44; A61D 7/00; A61M 31/00; A61M 2210/0662; A61P 27/16; A61P 31/00
See application file for complete search history.

(56) References Cited

U.S. PATENT DOCUMENTS

| | | | |
|---|---|---|---|
| 2005/0239722 A1* | 10/2005 | Albert | A61K 45/06 514/39 |
| 2007/0078116 A1 | 4/2007 | Lane | |
| 2010/0036000 A1 | 2/2010 | Lichter et al. | |
| 2013/0178801 A1 | 7/2013 | Branch et al. | |
| 2016/0058775 A1 | 3/2016 | Prasad et al. | |

OTHER PUBLICATIONS

Law Insider Dictionary. Therapeutic Agent definition. Retrieved from the Internet on Jan. 19, 2024, https://www.lawinsider.com/dictionary/therapeutic-agent. (Year: 2024).*
PCT International Search Report and Written Opinion in International Application No. PCT/US2020/054770, dated Jan. 13, 2021, 11 pages.
Bensignore et al., "Comparison of an Antifungal Agent with a Mixture of Antifungal, Antibiotic and Corticosteroid Agents for the Treatment of *Malassezia* Species Otitis in Dogs," Veterinary Record, Feb. 2006, 158(6): 193-195.
EP Extended Search Report in European Application No. 20874331. 0, dated Sep. 22, 2023, 6 pages.
Veterinary Dermatology, "Plenary Session Abstracts: Thursday Morning, Jul. 26 Theme: Allergy," Veterinary Dermatology, Jan. 1, 2012, 23(1): 2-104.

* cited by examiner

*Primary Examiner* — Amy C Bonaparte
*Assistant Examiner* — Lauren Wells
(74) *Attorney, Agent, or Firm* — DLA Piper LLP (US)

(57) ABSTRACT

The present invention relates to a formulation and method for treating an ear infection, especially otomycosis and otitis externa, by administering a one-time only treatment comprising an antibiotic, antifungal, and an anti-inflammatory in a thick, otic carrier. In one embodiment, the formulation comprises a therapeutically effective amount of active ingredients including a marbofloxacin, terbinafine and/or clotrimazole and dexamethasone.

16 Claims, No Drawings

OTIC FORMULATIONS, METHODS AND DEVICES

CROSS-REFERENCE TO RELATED APPLICATIONS

This application claims benefit of priority under 35 U.S.C. § 119(e) of U.S. Provisional Patent Application Ser. No. 62/914,301, filed Oct. 11, 2019, the contents of which is incorporated herein by reference in its entirety.

BACKGROUND OF THE INVENTION

Field of the Invention

The invention relates to an anti-fungal/anti-bacterial/anti-inflammatory formulation for treating ear infection, especially chronic otitis, and methods and devices for delivering the formulation.

Background Information

Ear infections, especially fungal ear infections, are common ear disorders often occurring in warm and humid climates. Fungal otitis externa is a fungal infection of the external auditory canal and associated complications. It has been reported that as high as 30.4% of otitis externa patients exhibit symptoms of fungal otitis or inflammatory conditions of the ear.

Common symptoms of ear fungal infection include otalgia, otorrhea, hearing loss, aural fullness, pruritus and tinnitus. Several factors that may cause or enhance the rate of fungal infection include humid climate, the presence of cerumen (ear wax) acting as a support for fungal growth, configuration of the ear canal, weak immune function, diabetes, increased use of ototopical antibiotics, prolonged use of broad-spectrum antibiotics, use of systemic steroids, pregnancy, hearing aids with occlusive molds, trauma and bacterial infections.

Common fungi that cause otitis externa are *Aspergillus niger* and *Candida albicans*, and treatment thereof can be tailored against these fungi. Other fungi may also cause otitis externa and can also be treated by respective therapeutic agents. It is debatable whether identification of the causal agent is necessary for determining the appropriate treatment. One school of thought believes that the treatment should be based on the susceptibility of the identified species, whereas others believe that the treatment should based on efficacy and characteristics of the drug regardless of the causing microbes. An experienced Ear, Nose and Throat physician (ENT) can now routinely treat fungus without cultures, mostly by identifying the characteristic fungal elements grossly on exam and apply topical acidifying agents or specific antifungals. Thus, practitioners can identify the organism, or just treat the likely organisms empirically according to best practices, as desired.

Currently, there are four main classes of drugs for the treatment of fungal infections, including polyenes, triazoles, nucleoside analogs and enchinocandins. The mechanism of action of the polyenes and triazoles families involves an essential chemical component called ergosterol found in the fungal cell membrane. The drug binds to ergosterol and creates a polar pore in the fungal membranes, which results in the leaking of ions and other molecules from within the cell, which in turn kills the cell. The nucleoside analogs interfere with nucleotide synthesis, which prevents proper energy production, metabolism and signaling of the cell. Echinocandins are a novel class of anti-fungal agents, acting by interfering with cell wall biosynthesis. However, echinocandins are known to be embryotoxic, and dose adjustment is required for patients having liver diseases.

To date, most reported treatment involves a solution, cream, powder or ointment to be topically applied multiple times for a period of time from one week to one month. The prolonged treatment regimen causes inconvenience to the patients because either they have to visit a primary care physician or otolaryngologist multiple times, or for self-administered drugs, patients often forget to apply the drugs according to instruction, resulting in secondary proliferation of fungus and bacteria that may further extend the treatment period. In addition, many drugs do not have complete efficacy for infection caused by multiple agents, and this can again prolong treatment times. Moreover, pure liquid form of drugs, such as ear drops, are less desirable for treating chronic otitis externa especially because the liquids egress from the ear canal very rapidly, and not all infected areas within the ear canal can be reached by the liquid because of gravity, especially in the upper half of the ear canal. Creams and ointments, in contrast, often remain in the ear and then have to be removed by the ENT.

U.S. Pat. No. 7,220,431 discloses a method for administering a pharmacological agent to the middle ear of a mammal by applying a formulation to the tympanic membrane of the mammal. The method does not teach how to treat an infection occurred at the auditory canal, such as otitis externa. The formulation is characterized by having a viscosity of less than 100,000 cps, and the formulation forms a gel after application to the tympanic membrane. However, the practical application of this patent may be problematic because once the ear canal is occluded, additional ear drops cannot be introduced. In addition, the solidified gel can be hard to remove by the patients after the infection symptoms are resolved. If the solidified gel remains too long within the ear canal after releasing all the active ingredients, recurrence of fungal and bacterial infection is likely.

U.S. Pat. No. 8,030,297 discloses a method for treating otic disorders selected from Meniere's disease, autoimmune ear disease, otitis media, acoustic trauma induced sensorineural hearing loss, drug-induced sensorineural hearing loss, sensorineural hearing loss, idiopathic sensorineural hearing loss, vertigo, and tinnitus. The method requires intratympanic administration of a pharmaceutical composition comprising a thermoreversible aqueous gel having 16% to 21% by weight of polyoxypropylene and polyoxyethylene and from 1 mg/ml to 70 mg/ml of a multiparticulate anti-inflammatory corticosteroid. The "intratympanic" administration and the targeted disorders make it clear that this patent does not treat otitis externa. Also, the patent does not teach the use of any antifungal agent for treating fungal infection.

There are also a couple of veterinary products available for animal use. POSATEX OTIC SUSPENSION™ by Intervet®/Schering-Plough Animal Health® contains Orbifloxacin, Mometasone Furoate Monohydrate and Posaconazole in a suspension. However, it has limited efficacy (*Pseudomonas aeruginosa* and the yeast *Malassezia pachydermatis*) and the orbofloxacin is only approved for use in dogs. Further, it is required to be used daily for 7 consecutive days.

TRI-OTIC™ by Med-Pharmex® contains Gentamicin Sulfate, Betamethasone Valerate, and Clotrimazole. However, this formula too requires twice daily application into the ear canal for 7 consecutive days, and has limited efficacy (*Malassezia pachydermatis*, formerly *Pityrosporum canis*, and/or bacteria susceptible to gentamicin).

There are also a few combinations approved for use in humans, but all are of very limited efficacy. CIPRODEX® by Alcon® is 0.3% ciprofloxacin and 0.1 in a suspension (0.3% ciprofloxacin 0.1% dexamethasone). However, it has no efficacy against fungus, and is directed for twice daily use for seven days. CIPRO HC® is a similar formulation containing ciprofloxacin and hydrocortisone and has the same limitations. CORTISPORIN®, available generically, contains neomycin and polymyxin B sulfates and hydrocortisone otic solution, but has the same limitations, and requires 3-4 applications a day for up to 10 days.

Therefore, there is still a need for a medical formulation and method for treating fungal ear infections, such as otomycosis and otitis externa, that requires only a single administration and yet is still capable of eradicating a spectrum of fungal and bacterial infections and the coincident inflammation. There is a particular need for a formulation that is capable of maintaining the active agents within the ear canal of a patient such that only a single dose of the formulation is required to achieve a high cure rate of otomycosis and otitis externa.

SUMMARY OF THE INVENTION

The present disclosure relates to formulations, methods and devices for treating chronic otitis externa that requires only a one-time administration, while retaining very high efficacy against a broad spectrum of microorganisms, including fungus and bacteria. The formulation comprises a therapeutically effective amount of one or more antibacterial agents, one or more antifungal agents, and one or more anti-inflammatory agents, together with a thickened base that egresses from the ear in less than 7 days.

Preferred embodiments include marbofloxacin, dexamethasone and either or both of terbinafine and clotrimazole. Together, these make up the active ingredients that eradicate a broad spectrum of fungal infections and any accompanying bacterial infection and inflammation. The formulation may also benefit from combination with anesthetics or analgesics. For example, benzocaine, which is already approved for otic use, can provide significant pain relief.

With the single-dose formulation of the present invention, complications due to patients' non-compliance in not following dosing instructions can be eliminated. Additionally, the optimal approach of applying the Active Pharmaceutical Ingredients ("APIs") directly to the infected area result in less bacterial community resistance due to a considerably lower one-time dose, thereby keeping bacterial resistance to a minimum.

Additionally, the use of a viscous carrier in the formulation makes it possible for the formulation to remain in viscous form once it is administered inside the ear canal and heated up by body temperature. Because of the high viscosity, the entire therapeutic formulation remains in contact with the infected ear canal for a prolonged time and the active ingredients can be continuously released for at least two, three, four or more days.

In embodiments, formulations include the following.

TABLE A

| Otic Formulations (% w/w) |
| --- |
| 1.5-2.0% marbofloxacin, 1.5-2.0% terbinafine, 0.1-0.25% corticosteroid, plus thickener and mineral oil. |

TABLE A-continued

| Otic Formulations (% w/w) |
| --- |
| 1.5-2.0% marbofloxacin, 1.0-2.0% clotrimazole, 0.1-0.25% corticosteroid, plus thickener and mineral oil. |
| 1.5-2.0% marbofloxacin, 1.5-2.0% terbinafine, 0.1-0.25% dexamethasone, plus thickener and mineral oil. |
| 1.5-2.0% marbofloxacin, 1.0-2.0% clotrimazole, 0.25% dexamethasone, plus thickener and mineral oil. |
| 1.5-2.0% marbofloxacin, 1.5-2.0% terbinafine, 0.1-0.25% dexamethasone, plus mineral oil and paraffin. |
| 1.5-2.0% marbofloxacin, 1.0-2.0% clotrimazole, 0.1-0.25% dexamethasone, plus mineral oil and paraffin. |
| 1.5-2.0% marbofloxacin, 1.5-2.0% terbinafine, 0.1-0.2% dexamethasone, 78-81% mineral oil and 16-19% paraffin. |
| 1.5-2.0% marbofloxacin, 1.0-2.0% clotrimazole, 0.1-0.2% dexamethasone, 78-81% mineral oil and 16-19% paraffin. |
| 1.7-1.8% marbofloxacin, 1.2-2.0% terbinafine, 0.1-0.25% dexamethasone, 79-80% mineral oil and 17-18% paraffin. |
| 1.5-2.0% marbofloxacin, 1.5-5.0% terbinafine, 0.1-0.3% corticosteroid, plus thickener and mineral oil. |
| 1.5-2.0% marbofloxacin, 1.5-5.0% terbinafine, 0.1-0.3% dexamethasone, plus thickener and mineral oil. |
| 1.5-2.0% marbofloxacin, 1.5-5.0% terbinafine, 0.1-0.3% dexamethasone, plus paraffin and mineral oil. |
| 1.5-2.0% marbofloxacin, 1.5-5.0% terbinafine, 0.1-0.3% dexamethasone, 65-75% mineral oil and 20-30% paraffin. |
| 1.5-2.0% marbofloxacin, 2.0-4.0% terbinafine, 0.1-0.3% dexamethasone, 65-75% mineral oil and 20-30% paraffin. |
| 1.5-2.0% marbofloxacin, 2.0-4.0% terbinafine, 0.1-0.3% dexamethasone, 70-72% mineral oil and 23-26% paraffin. |

In another aspect of the invention, is the use of the herein described combination of compounds to manufacture a therapeutic to treat the herein described ear infections.

Another aspect of the invention, is a method of manufacturing a therapeutic agent, the method comprising blending the herein described combination of compounds together with a viscous carrier to make one of the herein described therapeutic compositions.

Another aspect of the invention is a kit comprising the herein described compositions packaged together with instructions for single administration use to treat ear infections.

Another aspect of the invention, is a kit comprising the herein described compositions packaged inside, together with instructions for single administration use to treat ear infections.

The single use otic formulation for the ear canal includes a viscous carrier. The carrier can be any ontologically acceptable materials with the desired viscosity and that achieves the goal of maintaining the formulation within the ear canal for a prolonged period of time, preferably at least 2, 3, 4, 5, 6, 7, 8, 9 days or longer. Choosing different carriers may change the physical nature of the formulation, but not the therapeutic effect. For example, a person skilled in the art may so choose the carrier to make the formulation in fluid, foam, cream, ointment, or other ontologically acceptable form.

Thickeners can be completely natural, like waxes, and also synthetic or semi-synthetic polymers and the like, including polysaccharides, proteins, alcohols, silicones or waxes. Suitable thickeners may include bees wax, candelilla wax, carnauba wax, paraffin, Ozokerite wax, cetyl alcohol, corn starch, glyceryl stearate, guar gum, gum Arabic, xanthan gum, lanolins, microcrystalline wax, acrylate polymers, poly-alphaolefins, HE-Cellulose, PEG-150 Distearate, sorbitol, stearic acid, stearyl palmitate, Poloxamer 407, and the like.

The preferred thickeners are water insoluble or have low water solubility for longevity, and are not ototoxic. Preferred carriers include a combination of mineral oil and thickener, such as the proprietary blend of low density polyethylene known as PCCA Plasticized™ (PCCA US, TX, Cat. No. 30-3211). Even more preferred is a blend 10-25%, 15-21% or about 17% or 18% United States Pharmacopoeia (USP) or National Formulary (NF) paraffin brought to 100% (ww) with USP or NF mineral oil.

The carrier is characterized in that it remains a thick fluid in the preferred embodiment for human or other mammalian patients having approximately 10,000, 20,000, 30,000, 40,000, 50,000, 60,000, or 70,000 cPs after being applied to a subject's ear canal and heated by the body temperature of 37° C. At least 10,000, 20,000, 30,000 or 40,000 cPs thickness is desired, preferably at least 10,000, 15,000, 20,000, 30,000, 40,000, 45,000, 50,000, 55,000 or 60,000 cPs, however, variations can be accommodated. If the formulation is too thick, it will not egress, and thus formulations over 80,000 cPs are less desirable, and preferably less than 70,000 cPs. The dynamic A (absolute) viscosity is to be ascertained at 37° C. according to ATSM D-2394.

Although thick, the formulation remains a flowable fluid that can be applied by an injection unit, such as a syringe and a needle. The viscous fluid stays within the ear canal and remains in contact with the infected portion of the tissue. This allows the active ingredients within the formulation to be continuously released for a prolonged period of time, preferably at least 3 days, more preferred at least 4 days, and ideally 5 days, or even 6-7 days, thus continuously treating the fungal and bacterial infections, as well as the inflammation accompanied with the infections. More to the point, since the thick fluid will be in place for a prolonged period of time, the continuously released active ingredients will also maintain the hygiene within the ear canal by preventing the proliferation of fungi and bacteria. Additionally, the viscous nature of the formulation allows it to gradually egress from the ear canal (or be absorbed) after symptoms are resolved.

In another embodiment of the invention, the carrier can be a thinner liquid formulation and the formulation used to treat of acute otitis media using tympanostomy tubes (AOMT). This would allow the use of a liquid form of the product to cross the tympanic membrane through a myringotomy tube in cases of ear drainage. Such carriers are described, for example in U.S. Pat. Nos. 7,220,431 and 8,030,297. However, some drugs suitable for use in the external ear canal may not be suitable for use across the membrane, and each will have to be tested for suitability.

Another aspect of the invention provides a method for treating an ear infection. The method comprises the step of applying, typically only once or possibly twice, a formulation into the ear canal of a mammal, wherein the formulation is as described herein.

In yet another aspect of the present invention, a therapeutic kit for treating ear infections is provided, comprising an injection unit having a storage compartment fluidly coupled to a delivery component, such as a small tube or syringe, and a therapeutic formulation stored within the storage compartment. The therapeutic formulation is as described herein. The device is preferably a single use device, disposed of after use. In other embodiments, the storage compartment allows for multiple doses, but the delivery component is disposable.

DETAILED DESCRIPTION OF THE INVENTION

The present disclosure provides a novel formulation and method for treating ear fungal infections, especially otitis externa. The formulation and method of the present invention makes it possible to treat and even eradicate the chronic otitis externa by one-time only administration of the formulation to the ear canal.

The disclosure provides a novel formulation for treating fungal ear infection, comprising an antifungal, an antibiotic and an anti-inflammatory agent in a thick base of 10-80,000 cPs at ear or body temperature.

As used herein, "ear infection" means fungal and/or bacterial infection in the ear. The location of the infection is primarily the auditory canal. In an embodiment, the term ear infection includes otomycosis, chronic and acute otitis externa.

As used herein, "active ingredient" means the substance of a pharmaceutical drug that has therapeutic effect against the disorder to be treated.

As used herein, "corticosteroid" means a class of steroids having anti-inflammatory effect that may include, but are not limited to, amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and combinations thereof.

As used herein, "thickener" means optically acceptable additives that increase viscosity of the formulation. The thickener may make the overall formulation as auris-acceptable viscous fluid when the temperature rises to body temperature. Examples of thickeners that can be used in the present invention include, but not limited to, low-density polyethylene, poloxamers, waxes and the combination thereof. Mineral oil can be added to adjust the viscosity of the thickener. The thickener in the present invention preferably provides a formulation with a viscosity of approximately about 10-80,000 cPs at 37° C., about 10,000-80,000 cPs at 37° C., about 20,000-80,000 cPs at 37° C., or about 40,000-80,000 cPs at 37°, such as about 50,000-70,000 cPs at 37° C. or about 60,000-62,000 cPs at 37° C.

As used herein, "injection unit" means a unit that is capable of storing a therapeutic agent and injecting or delivering the therapeutic agent to a target area of a subject. Typical injection units include, but are not limited to, a syringe coupled with a needle or a tube, e.g., via a standard luer lock or luer connector. The needle or tube can be customized as described herein.

As used herein, "flowable" means a fluid having a viscosity less than 100,000 cPs at room temperature.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, special packaging, preservatives, antioxidants and the like. The active pharmaceutical ingredients are considered material.

When a drug is referred to by name herein, all active salts, isomers, and derivatives thereof are considered to be included.

All percentages are by weight, unless indicated otherwise.

In an embodiment, the disclosure provides a formulation for treating an ear infection in a mammal, the formulation comprising 0.01% to 5% by weight of marbofloxacin, 0.01% to 5% by weight of terbinafine and/or clotrimazole, 0.01% to 2.5% by weight of a corticosteroid, 10% to 70% by weight of thickener, and 30% to 90% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 1% to 3% by weight of terbinafine and/or clotrimazole, 0.1% to 0.3% by weight of a corticosteroid, 15% to 25% by weight of thickener, and 70% to 90% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 2% by weight of marbofloxacin, 1% to 2% by weight of terbinafine and/or clotrimazole, 0.1% to 0.25% by weight of a corticosteroid, 15% to 25% by weight of thickener, and 70% to 90% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 1% to 3% by weight of terbinafine and/or clotrimazole, 0.1% to 0.3% by weight of a corticosteroid, 15% to 20% by weight of thickener, and 75% to 80% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 2% by weight of marbofloxacin, 1% to 2% by weight of terbinafine and/or clotrimazole, 0.1% to 0.25% by weight of a corticosteroid, 15% to 20% by weight of thickener, and 75% to 80% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 1% to 5% by weight of terbinafine, 0.1% to 0.3% by weight of a corticosteroid, 20% to 30% by weight of thickener, and 65% to 80% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 2% to 4% by weight of terbinafine, 0.1% to 0.3% by weight of a corticosteroid, 20% to 30% by weight of thickener, and 65% to 80% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 2% to 4% by weight of terbinafine, 0.1% to 0.3% by weight of a corticosteroid, 20% to 30% by weight of thickener, and 65% to 75% by weight of mineral oil. Other therapeutically appropriate bases can also be utilized in the present invention in place of the thickener without affecting the efficacy of the formulation.

In an embodiment, the disclosure provides a formulation for treating an ear infection in a mammal, the formulation comprising 1% to 3% by weight of marbofloxacin, 2% to 4% by weight of terbinafine, 0.1% to 0.3% by weight of a dexamethasone, 20% to 30% by weight of paraffin, and 65% to 75% by weight of mineral oil. Other therapeutically appropriate bases can also be utilized in the present invention in place of the thickener without affecting the efficacy of the formulation.

In an embodiment, the corticosteroid is selected from amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasone furoate, prednisolone acetate, triamcinolone acetonide, and the combination thereof. More preferably, the corticosteroid is dexamethasone, hydrocortisone, triamcinolone acetonide or the combination thereof.

In an embodiment, the carrier comprises mineral oil and a thickener. In one embodiment the thickener is paraffin and the carrier includes about 11-21% w/w or about 17% or 18% paraffin in mineral oil. In one embodiment the thickener is paraffin and the carrier includes about 20-30% w/w or about 24% or 25% paraffin in mineral oil. In one embodiment the thickener is paraffin and the carrier includes about 20-30% w/w or about 24% or 25% paraffin in about 65-80% w/w or about 71% or 72% mineral oil. In one embodiment the thickener is paraffin and the carrier includes about 22-26% w/w or about 24% or 25% paraffin in about 70-75% w/w or about 71% or 72% mineral oil. In one embodiment the thickener is paraffin and the carrier includes paraffin in about 65-80% w/w or about 70-75% mineral oil.

In an embodiment, the method for treating ear infection comprises the following steps: applying one time, a formulation of the disclosure into the ear canal of a mammal, wherein the formulation forms a gel after applying to the ear canal of the mammal, and wherein the gel releases the active ingredients continuously for at least 2, 3, 4, 5, 6, 7, 8 or 9 days. In some embodiments, before applying the formulation to the ear canal, the method further comprises the step of debriding infectious and inflammatory debris from the ear canal.

In another embodiment, the invention is a formulation for treating ear infection, comprising: one or more antifungal agents; one or more anti-bacterial agents; one or more anti-inflammatory agents; and a carrier having about 10-80,000 cPs at 37° C., about 10,000-80,000 cPs at 37° C., about 20,000-80,000 cPs at 37° C., or about 40,000-80,000 cPs at 37° C., wherein the carrier retains the active ingredients in an ear for 2-7 days and then egresses or is absorbed.

In an embodiment, the otic formulation, comprises marbofloxacin, terbinafine and dexamethasone in an aurally acceptable carrier. Preferably, 0.1-10% marbofloxacin, 0.1-10% terbinafine and 0.01-5% dexamethasone are used, most preferred is 1.5-2.0% marbofloxacin, 1.5-5.0% terbinafine, and 0.1-0.25% dexamethasone in a suitable carrier as described herein.

In an embodiment, the otic formulation, comprises marbofloxacin, clotrimazole and dexamethasone in an aurally acceptable carrier. Preferably, 0.1-10% marbofloxacin, 0.1-10% clotrimazole and 0.01-5% dexamethasone are used, most preferred is 1.5-2.0% marbofloxacin, 1.0-2.0% clotrimazole, and 0.1-0.25% dexamethasone in a suitable carrier as described herein.

In an embodiment, the suitable mammal that can be treated with the formulation and method of the present invention includes humans, canines, felines, bovines, ovines, porcines, equines, as well as other mammals commonly treated by veterinarians for ear infections.

The present disclosure further provides a therapeutic kit for treating ear infections. In one embodiment, the therapeutic kit comprises an injection unit as a syringe, needle or hollow tube, comprising a storage compartment for storing the drug formulation described herein. The tube or needle can be bent to any degree suitable for use, so long as it does not affect the dispensation of the therapeutic formulation.

The entire kit can be disposable, in which case the storage volume is small to hold the amount suitable for single dosage, for example, 1 to 1.5 ml, in order to prevent waste. Or alternatively, the kit can be used repeatedly until no therapeutic formulation is left, in which case the storage volume is large to hold multiple dosages, for example 10 to 30 ml. Volumes may change if the patients are not human, e.g., a larger dose may be required for dogs.

Preparing the formulation of the present invention can be performed with various compounding methods, as long as the final product has the desired characteristics, such as remaining flowable at both room temperature and body temperature, while remaining in the ear canal for a prolonged period of time and providing a continuous release of active ingredients.

The following ingredients are included in a formulation in one embodiment of the invention.

TABLE B

| Active Ingredient | Amount (% w/w) |
| --- | --- |
| Marbofloxacin | 1.5-1.9 |
| Terbinafine | 1.6-2.0 |
| Dexamethasone (micronized) | 0.1-0.25 |

TABLE B-continued

| Active Ingredient | Amount (% w/w) |
| --- | --- |
| Mineral Oil | 78-80 |
| Paraffin | 17-18 |
| | 100 total |

The following ingredients are included in a formulation in one embodiment of the invention.

TABLE C

| Active Ingredient | Amount (% w/w) |
| --- | --- |
| Marbofloxacin | 1.5-2.0 |
| Clotrimazole | 1.0-2.0 |
| Dexamethasone (micronized) | 0.1-0.25 |
| Mineral Oil | 78-80 |
| Paraffin | 17-18 |
| | 100 total |

The following ingredients are included in a formulation in one embodiment of the invention.

TABLE D

| Active Ingredient | Amount (% w/w) |
| --- | --- |
| Marbofloxacin | 1.7-1.8 |
| Terbinafine | 1.6-2.0 |
| Dexamethasone (micronized) | 0.1-0.25 |
| Mineral Oil | 78-79 |
| Paraffin | 17-18 |
| | 100tal |

TABLE E

| Active Ingredient | Amount (% w/w) |
| --- | --- |
| Marbofloxacin | 1.5-1.9 |
| Terbinafine | 2.7-3.3 |
| Dexamethasone (micronized) | 0.1-0.3 |
| Mineral Oil | 70-74 |
| Paraffin | 22-26 |
| | 100 total |

TABLE F

| Active Ingredient | Amount (% w/w) |
| --- | --- |
| Marbofloxacin | 1.5-1.9 |
| Terbinafine | 2.7-3.3 |
| Dexamethasone (micronized) | 0.1-0.3 |
| Mineral Oil | 71-72 |
| Paraffin | 23-24 |
| | 100 total |

In manufacture, marbofloxacin powder, clotrimazole or terbinafine powder, and dexamethasone powder may be measured according to respective weight and placed inside a mixing vessel, such as a flask.

The mineral oil may then be added and the combination mixed well. Finally, the thickener and an additional amount of mineral oil may be added to the vessel to make the final volume and mixed well. Additional mineral oil may be added to adjust the viscosity of the formulation.

In the methods described herein, an appropriate dosage level of active ingredients will generally be about 0.01 to about 50 mg/kg, such as, for example, about 0.25 to about 15 mg/kg per day, such as about 2.0 to about 14 mg/kg per day. Within this range the dosage of each active ingredient may be about 0.25 to 3.5 mg/kg, 0.25 to 14 mg/kg, 1.0 to 10 mg/kg, 1.5 to 10 mg/kg, 2.0 to 10 mg/kg, 2.5 to 8.0 mg/kg, 2.5 to 8 mg/kg, 2.5 to 7.0 mg/kg, 2.5 to 6.5 mg/kg, 2.5 to 6.0 mg/kg, 2.5 to 5.5 mg/kg, 2.5 to 5.0 mg/kg, 2.5 to 4.0 mg/kg, 2.5 to 3.5 mg/kg (including all intermediate dosages, such as 2.5, 2.6, 2.7, 2.8, 2.9, 3.0, 3.1, 3.2, 3.3, 3.4, 3.5, etc. mg/kg), in a single dosage form. In this form, the composition need only be administered by single application, one time for an entire course of treatment to clinically resolve an infection with up to 100% elimination.

It is anticipated that the formulations of the disclosure achieve at least 90, 91, 92, 93, 94, 95, 96, 97, 98, 99 or 100% cure rate. It is expected that patients administered the formulations will show at least 90, 91, 92, 93, 94, 95, 96, 97, 98, 99 or 100% cure in 2-27 days with most being clinically cured under 7, 14 or 27 days, and with complete egress of the base from the ear. Of course, the percentages of base ingredients can vary depending on the wax chosen, softer waxes needing a higher percentage.

As used herein, "clinical cure rate" refers to a substantial reduction of symptoms or total elimination of symptoms. In embodiments, an infection is resolved with efficacy greater than 90, 91, 92, 93, 94, 95, 96, 97, 98, 99 or up to 100%, within a duration of less than 1, 2, 3, 4, 5, 6, 7, 8, 9, 10, 11, 12, 13, 14, 15, 16, 17, 18, 19, 20, 21, 22, 23, 24, 25, 26 or 27 days after a single administration.

It is expected that a 1 ml dose of formulation is sufficient is most cases. It is to be noted that the volume may change as the type of mammal being treated changes, and a person of ordinary skilled in the art can easily adjust the amount to suit the treatment needs. Different amounts of the present formulation may be administered to the mammal's ear canal as readily appreciated by a person skilled in the art.

After debriding the infectious and/or inflammatory debris from the ear canal, an appropriate amount of a formulation from above may be administered to the infected ear canal such that all available space in the outer ear was filled. The formulations may be stored in a syringe or container before use, and can be stored at room temperature without deteriorating the therapeutic effect.

The application of the formulation is illustrated as follows. First the ENT doctor carefully places a hollow tube inside the patient's auditory canal. Upon pressing the plunger or storage unit, the therapeutic formulation can be dispensed into the auditory canal and remains therein. In embodiments, the tube is flexible and includes a rounded tip such that doctors can minimize possible scratching when applying the therapeutic formulation. The dispensed thick fluid will fill in the space within the auditory canal, thereby contacting the infected area therein while preventing secondary infection in the ear canal.

After administration of the formulation, each patient may be examined to ensure that the formulation remained within the ear canal. Cotton balls may be provided at the outer ear canal (conchal bowl) to catch egress, but no attempt was made to "plug" the ear canal. Follow-up examination may be performed between 7 to 14 days after initial treatment. Residue of the formulation is expected to be observed at day 14, indicating the formulation did maintain within the ear canal for as long as 14 days. Symptoms relief is expected to occur usually within three days, while hearing is expected to return to normal within 5 to 7 days after treatment.

An ideal anti-inflammatory for use in the formulation is dexamethasone or hydrocortisone.

The following examples are provided to further illustrate the advantages and features of the present invention, but they are not intended to limit the scope of the invention. While the examples are typical of those that might be used, other procedures, methodologies, or techniques known to those skilled in the art may alternatively be used.

Example I

Treatment of Otitis Externa in Dogs

This study evaluated the effectiveness and field safety of an otic formulation of the present invention over a period of thirty (30) days for the treatment of otitis externa in dogs. Twenty-four (24) dogs were enrolled in the study from two study sites, and all 24 were treated with a formulation as described in Table B. All 24 dogs were included in the safety evaluation, while 21 dogs were included in the efficacy evaluation.

Dogs enrolled in the study presented to the clinic with signs of otitis externa. On Day 0, a physical examination, including an aural and otoscopic exam, was conducted in order to verify an intact tympanic membrane, absence of foreign bodies and ear mites, and to assign a clinical score to the study ear based on erythema, exudate, swelling and ulceration. In order to be included in the study, the minimum clinical score had to be greater than or equal to 6. A hearing test was conducted, an ear swab was obtained for bacterial culture and fungal (yeast) identification, and the ear was cleaned with saline. The dogs were dosed by administering 1.0 mL of the IVP per infected ear. If both ears were infected, the right ear was designated as the study ear.

At the first follow-up visit on Day 7 (+2 days), aural and otoscopic exams were conducted to evaluate the ear and assign a clinical score. In addition, the owner was questioned regarding any adverse events observed.

At the second follow-up visit on Day 14 (±2 days), aural and otoscopic exams were conducted to evaluate the ear and assign a clinical score. In addition, the owner was questioned regarding any adverse events observed.

At the final follow-up visit on Day 30 (+3 days), a physical examination, including an aural and otoscopic exam, was conducted to evaluate the ear and to assign a clinical score. A hearing test was also conducted. For a case to be considered a clinical cure, the final clinical score had to be less than or equal to 3, along with no individual clinical score getting worse at the final visit. If clinical cure was not achieved, an ear swab was obtained for bacterial culture and fungal (yeast) identification.

Based on clinical scores, clinical cures were obtained in 13 dogs by day 30 with at least 9 showing clinical cure by day 7. The number of clinical cures is expected to increase with the use of the formulations shown in Table E and Table F. There were both no serious adverse events or adverse events directly attributable to administration of the formulation, which demonstrated the safety of this formulation.

While preferred embodiments of the present invention have been shown and described herein, such embodiments are provided by way of example only. Various alternatives to the embodiments can be optionally employed without deviating from the spirit of the present invention. The scope of the invention is defined by the following claims.

What is claimed is:

1. An otic formulation comprising:
   a) therapeutic agents consisting of:
      i) about 1.5% to 1.9% w/w of marbofloxacin;
      ii) about 1.6% to 2.0% w/w of terbinafine or salts thereof; and
      iii) about 0.1% to 0.25% w/w of dexamethasone; wherein the formulation further comprises
   b) about 78% to 80% w/w mineral oil; and
   c) about 17% to 18% w/w paraffin.

2. The formulation of claim 1, wherein the formulation is in a flowable fluid form that can be delivered to an ear canal of a mammal.

3. The formulation of claim 2, wherein upon introduction into the ear canal the formulation remains in the ear canal for at least 3 days releasing the therapeutic agents.

4. The formulation of claim 1, wherein the formulation has a viscosity of about 10-80,000 cPs at 37° C.

5. An otic formulation, comprising:
   a) therapeutic agents consisting of:
      i) about 1.5% to 1.9% w/w of marbofloxacin;
      ii) about 1.6% to 3.3% w/w of terbinafine or salts thereof; and
      iii) about 0.1% to 0.3% w/w of dexamethasone; wherein the formulation further comprises
   b) about 17% to 26% w/w of wax; and
   c) about 70% to 80% w/w of mineral oil.

6. The formulation of claim 5, wherein after applying to an ear canal of a mammal having an ear infection, the formulation remains in the ear canal and has a viscosity of about 10-80,000 cPs at 37° C.

7. The formulation of claim 6, wherein upon introduction into the ear canal the formulation remains in the ear canal releasing the active ingredients for 2-7 days, and thereafter is not found in the ear canal.

8. The formulation of claim 7, wherein the formulation comprises about 1.50% to 1.9% w/w of marbofloxacin, about 2.7% to 3.3% w/w of terbinafine, about 0.1% to 0.3% w/w of dexamethasone, about 22% to 26% w/w of wax, and about 70% to 74% w/w of mineral oil.

9. The formulation of claim 8, wherein the formulation is for single treatment and has a clinical cure rate of at least 90% within a duration of less than 27 days.

10. An otic formulation, comprising therapeutic agents consisting of about 1.5% to 1.9% w/w of marbofloxacin, about 1.6% to 3.3% w/w of terbinafine or salts thereof and about 0.1% to 0.3% w/w dexamethasone in an aurally acceptable carrier, the carrier having about 10-80,000 cPs at 37° C., wherein the carrier retains the marbofloxacin, the terbinafine, and the dexamethasone wherein the formulation further comprises an ear for 7-14 days and then egresses or is absorbed, and wherein the formulation is for single treatment and has a clinical cure rate of at least 90% within a duration of less than 27 days.

11. An otic formulation comprising:
   a) therapeutic agents consisting of:
      i) about 1.5% to 1.9% w/w of marbofloxacin;
      ii) about 2.7% to 3.3% w/w of terbinafine or salts thereof; and
      iii) about 0.1% to 0.3% w/w of dexamethasone; wherein the formulation further comprises
   b) about 70% to 74% w/w mineral oil; and
   c) about 22% to 26% w/w paraffin.

12. An otic formulation comprising:
   a) therapeutic agents consisting of:
      i) about 1.5% to 1.9% w/w of marbofloxacin;
      ii) about 2.7% to 3.3% w/w of terbinafine or salts thereof; and wherein the formulation further comprises
      iii) about 0.1% to 0.3% w/w of dexamethasone;
   b) about 71% to 72% w/w mineral oil; and
   c) about 23% to 24% w/w paraffin.

13. A therapeutic kit comprising an injection unit comprising a storage compartment fluidly coupled to a delivery component, and a formulation of claim 1 stored within the storage compartment.

14. A method for treating an infection in an ear canal of a mammal, comprising applying a single dose of the formulation of claim 1 into the ear canal of a mammal with an ear infection.

15. The method of claim 14, wherein the ear infection is clinically resolved within a duration of less than about 27 days.

16. The method of claim 14, wherein the mammal is a human, canine or feline.

* * * * *